(12) United States Patent
Eckhouse et al.

(10) Patent No.: US 8,876,809 B2
(45) Date of Patent: Nov. 4, 2014

(54) HAIR REMOVAL APPARATUS FOR PERSONAL USE AND THE METHOD OF USING SAME

(75) Inventors: Shimon Eckhouse, Haifa (IL); Tuvia Dror Kutscher, Shoham (IL)

(73) Assignee: Syneron Medical TD, Yoqneam (IL)

( * ) Notice: Subject to any disclaimer, the term of this patent is extended or adjusted under 35 U.S.C. 154(b) by 1099 days.

(21) Appl. No.: 12/355,749

(22) Filed: Jan. 16, 2009

(65) Prior Publication Data

US 2010/0198134 A1 Aug. 5, 2010

Related U.S. Application Data

(60) Provisional application No. 61/021,723, filed on Jan. 17, 2008, provisional application No. 61/045,282, filed on Apr. 16, 2008.

(51) Int. Cl.
| | |
|---|---|
| A61B 18/18 | (2006.01) |
| A61F 2/00 | (2006.01) |
| B26B 19/42 | (2006.01) |
| B26B 21/48 | (2006.01) |
| A45D 26/00 | (2006.01) |
| B26B 19/46 | (2006.01) |
| A61B 18/20 | (2006.01) |
| A61B 18/00 | (2006.01) |

(52) U.S. Cl.
CPC ............... B26B 19/46 (2013.01); B26B 19/42 (2013.01); B26B 21/48 (2013.01); A61B 18/18 (2013.01); *A61B 2018/00476* (2013.01); *A61B 2018/00029* (2013.01); A45D 26/00 (2013.01); *A61B 2018/1807* (2013.01); *A61B 2018/00452* (2013.01); A61B 18/203 (2013.01)
USPC ............................................. 606/9; 607/101

(58) Field of Classification Search
CPC ....... A45D 26/00; A61B 18/203; B26B 19/42; B26B 19/46; B26B 19/48
USPC ............ 606/9, 32, 36–39, 41–43; 607/88–91, 607/96, 98, 101, 145
See application file for complete search history.

(56) References Cited

U.S. PATENT DOCUMENTS

| | | | | |
|---|---|---|---|---|
| 3,088,205 | A * | 5/1963 | Ellis | 30/34.05 |
| 5,582,476 | A * | 12/1996 | Hansen | 362/115 |
| 5,735,844 | A * | 4/1998 | Anderson et al. | 606/9 |
| 6,288,498 | B1 * | 9/2001 | Cheng | 315/185 S |
| 6,406,157 | B1 * | 6/2002 | Audet | 362/115 |
| 6,533,775 | B1 * | 3/2003 | Rizoiu | 606/9 |
| 7,234,239 | B2 * | 6/2007 | Saito et al. | 30/41 |
| 2002/0120256 | A1 * | 8/2002 | Furuno et al. | 606/9 |
| 2003/0032950 | A1 * | 2/2003 | Altshuler et al. | 606/9 |
| 2007/0239143 | A1 * | 10/2007 | Altshuler et al. | 606/9 |
| 2007/0271714 | A1 * | 11/2007 | Adam et al. | 15/22.2 |

* cited by examiner

*Primary Examiner* — Lynsey Crandall
*Assistant Examiner* — Nathan J Jenness
(74) *Attorney, Agent, or Firm* — Smith Risley Temple Santos LLC; Gregory Scott Smith

(57) ABSTRACT

Hair or partial hair removal system and hair growth deterrent that includes mechanical process for cutting, plucking or shaving hair follicles, along with pre and/or post skin treatment techniques. The skin treatment techniques can include the application of energy to the skin surface before, after and/or during the application of the mechanical process. Such techniques include the application of heat and/or energy from illumination sources and/or RF emitters. Further skin treatment techniques include the application of solutions before, after and/or during the mechanical process and/or the application of heat and/or energy. Overall, the system operates to treat an area of skin to facilitate the removal of all or a portion of hair, retard further growth, and recovery of skin surface.

17 Claims, 19 Drawing Sheets

DETAIL I-I.

HAIR REMOVAL APPARATUS FOR PERSONAL USE AND THE METHOD OF USING SAME

CROSS-REFERENCE TO RELATED APPLICATIONS

This application is a non-provisional application being filed under 37 CFR 1.53(b) and 35 USC 111, claiming the benefit of the priority date of the U.S. Provisional Application for patent that was filed on Jan. 17, 2008 and assigned Ser. No. 61/021,723, and of the U.S. Provisional Application for patent that was filed on Apr. 16, 2008 and assigned Ser. No. 61/045,282, both of which are hereby incorporated by reference.

BACKGROUND

The method and apparatus disclosed herein are related to the field of personal cosmetic procedures and in particular to hair removal procedures.

External appearance is important to practically everybody. In recent years, methods and apparatus have been developed for different cosmetic treatments. Among these cosmetic treatments includes hair removal, treatment of vascular lesions, skin rejuvenation, as well as others. In some of these treatments, the skin surface is illuminated by visible or infra red (IR) radiation, generally termed optical radiation, to heat lower tissue volumes to a sufficiently high temperature so as to achieve a desired effect, which is typically in the range of 38-80 degrees Celsius. One such desired effect may include weakening of the hair follicle or root destruction. Another desired effect may include hair re-growth retardation, which is typically achieved by illumination of earlier depilated skin surface by laser, LED, Xenon lamp, Intense Pulsed Light (IPL), or incandescent lamp radiation, generally termed optical radiation. The optical radiation may have a single wavelength, such as is the case with lasers, or several wavelengths as is the case for incandescent lamps. The wavelengths are selected to be optimal for the color of the contrasted component of the treated skin segment and are typically in the range of 400 to 1800 nm.

Presently, a number of Radio Frequency (RF) based methods for treatment of deeper skin or tissue layers have been developed and are available. In these methods, electrodes are applied to the skin and an RF voltage in pulse or continuous waveform (CW) is applied across the electrodes. The properties of the RF voltage are selected to generate RF induced current in a volume of tissue to be treated. The current heats the tissue to the required temperature, which is typically in the range of 38-80 degrees Celsius.

However, the above-described equipment that utilizes electrodes is both costly and bulky. Further, such equipment is typically operated in an ambulatory set-up by a qualified operator and frequently requires the presence of medical personnel specialized in such treatments. Therefore, there is a need in the art for a small size, low cost, and safe to use apparatus that may be operated by the user, enabling him/her to conduct skin treatment and get results similar or identical to those provided by professional equipment used for skin treatments.

Glossary

Several terms are utilized throughout this disclosure. The definitions for these terms are provided here for convenience.

The term "illumination sources" and "light sources" as used in the present disclosure has the same meaning and includes sources of visible and invisible infrared radiation.

As used herein, the term "hair removal" includes partial or complete hair removal from the treated skin surface as well as hair re-growth retardation.

The term "skin surface" relates to the most external skin layer, which may be stratum corneum.

The term "tissue" relates to skin layers located below the stratum corneum. The layers may be located immediately below the stratum corneum and as deep as 6 or even 7 mm below the stratum corneum.

BRIEF SUMMARY

Various embodiments are directed towards an apparatus, system or method of providing complete or partial hair removal and hair growth deterrent. The embodiments may include various elements that may include, but are not limited or required in all embodiments. Some of these elements are: (a) a mechanical process for cutting, plucking or shaving hair follicles; (b) integrated and/or removable cartridges to provide the application of heat and/or energy to the skin surface before, after and/or during the application of the mechanical process; (c) further skin treatment techniques including the application of solutions before, after and/or during the mechanical process and/or the application of heat and/or energy. Overall, the various embodiments operate to treat an area of skin to facilitate the removal of all or a portion of hair, retard further growth, and recovery or health maintenance of the skin surface.

BRIEF DESCRIPTION OF THE SEVERAL VIEWS OF THE DRAWING

The disclosure is provided by way of non-limiting examples only, with reference to the accompanying drawings, in which like reference characters refer to the same parts throughout the different views. The drawings are not necessarily to scale, emphasis instead being placed upon illustrating the principles of the method.

DETAILED DESCRIPTION OF EXEMPLARY EMBODIMENTS

The principles and execution of the apparatus and the method described thereby may be understood with reference to the drawings and the accompanying description of non-limiting, exemplary embodiments.

Figure 1:
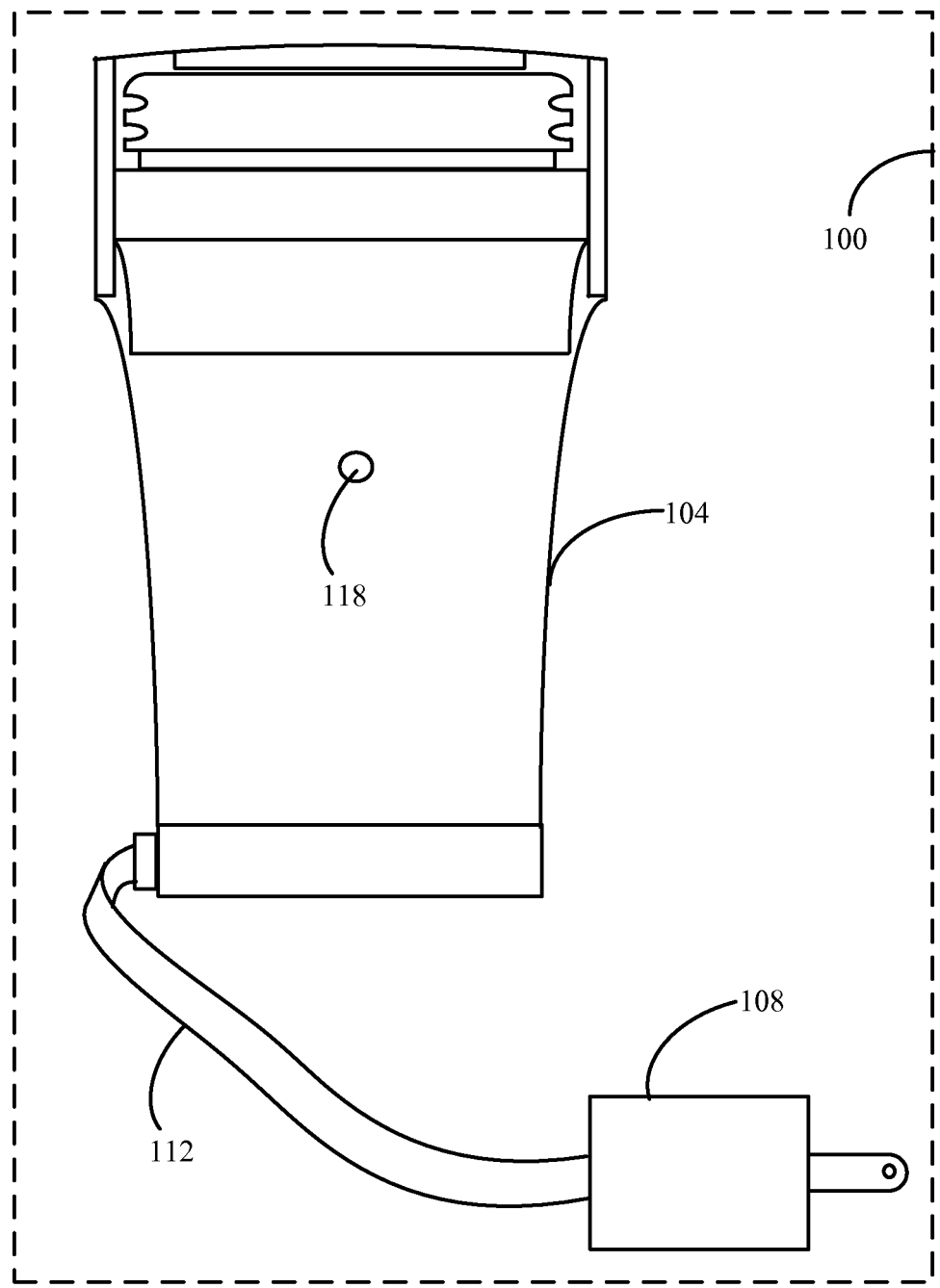
FIG. 1 is a schematic illustration of an exemplary embodiment of the apparatus for personal use for hair removal.

Reference is made to FIG. 1, which is a schematic illustration of an exemplary embodiment of the apparatus for personal hair removal. Apparatus 100 comprises an applicator 104 adapted for sliding movement on a subject skin, a charging device 108, and a harness 112 connecting between applicator 104 and charging device 108. Harness 112 enables electric communication between applicator 104 and charging device 108. Apparatus 100 may receive power supply from a regular electric supply network receptacle, or from a rechargeable or regular battery. LED 118 indicates operational status of applicator 104.

Figure 2A:
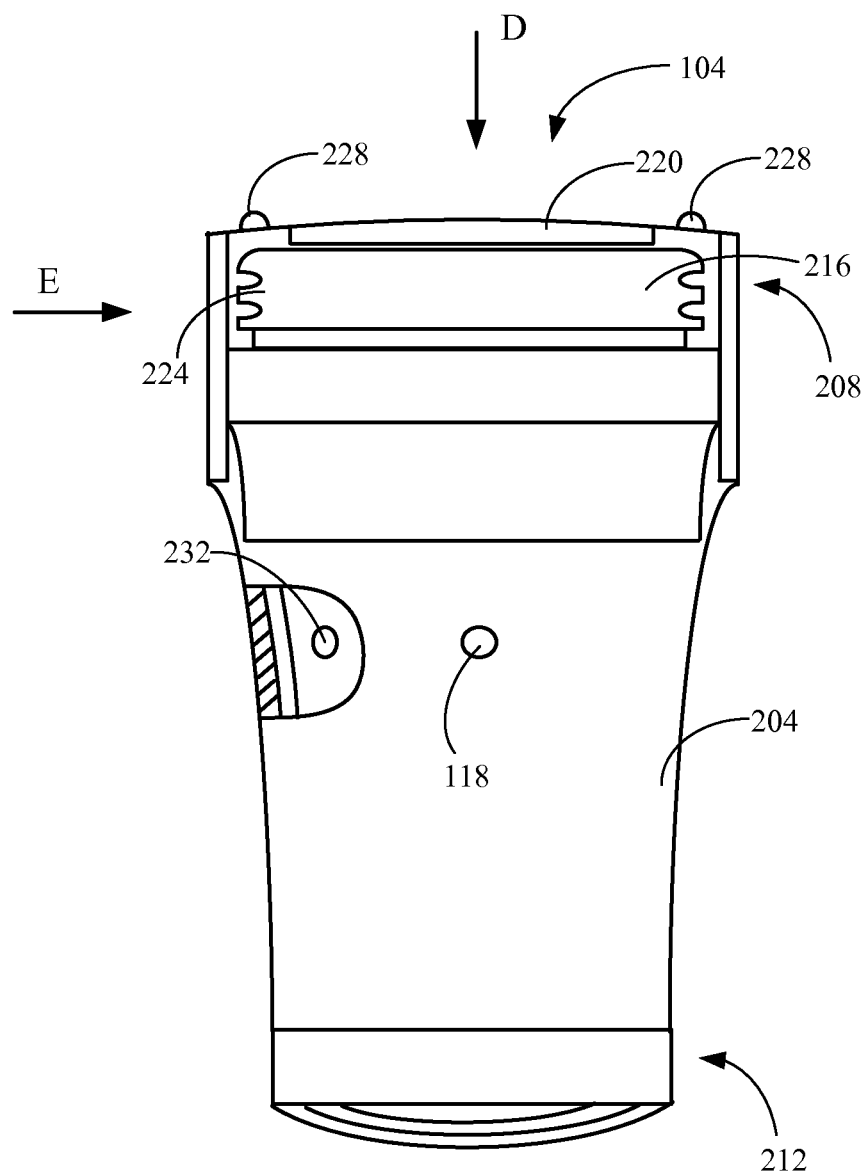
FIGS. 2A-2C are schematic illustrations of the first exemplary embodiment of the applicator of the apparatus of FIG. 1.
Figure 2B:
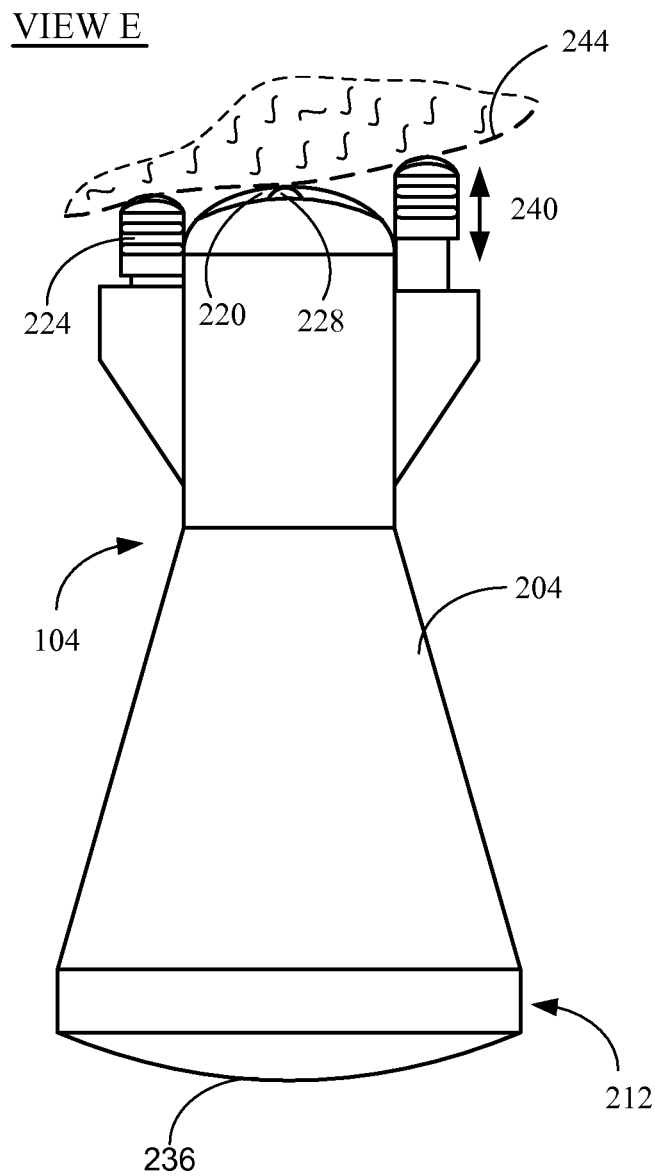
Figure 2C:
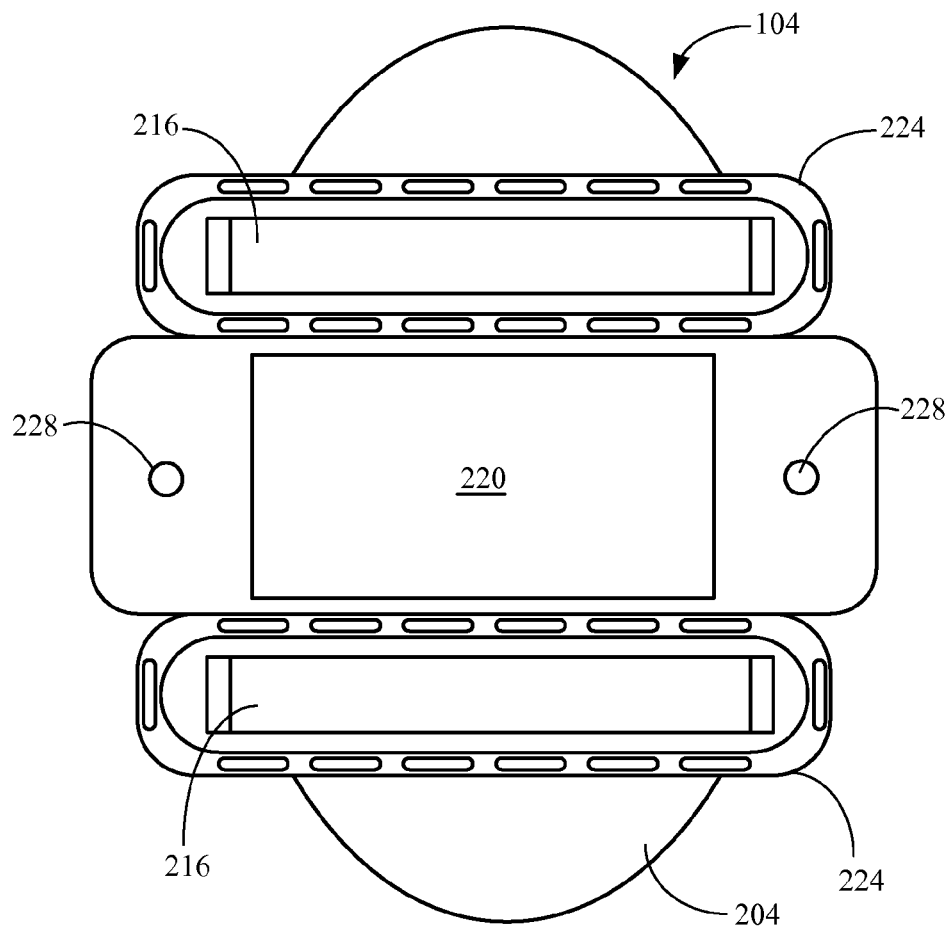

FIG. 2A is a first side planer view of a first exemplary embodiment of the applicator of the apparatus of FIG. 1. FIG. 2B is a second side planer view in the direction of arrow E of FIG. 2A of the first exemplary embodiment of the applicator of the apparatus of FIG. 1. FIG. 2C is a top planer view in the direction of arrow D of FIG. 2A of the first exemplary embodiment of the applicator of the apparatus of FIG. 1. The series of drawings represented in FIGS. 2A-2C may be referred to collectively as FIG. 2. Applicator 104 (FIG. 2A) is shown to include an ergonomically designed casing 204 which fits the hand, having a first end 208 and a second end 212. One or more illumination sources 216, at least one hair removal mechanism 220, and at least one contact to skin sensing mechanism shown as micro switches 228 for activating illumination sources 216 and a hair removal mechanism 220. Micro switches 228 are located at the first end 208 and are activated by slight pressure developed by application of applicator 104 to skin (not shown). When depressed, micro switches 228 enable one or more illumination sources 216 and other electric and electronic circuits of applicator 104. In one embodiment, illumination sources 216 and other electric and electronic circuits may each be operated independently and have their own ON and OFF switch mechanisms, for example, RF current sensing mechanism. It will also be appreciated that in some embodiments, other sensor mechanisms may also be utilized such as capacitive coupling, ground detection, a mechanical on/off switch operated by a user as well as other techniques.

The illumination sources 216 may include a variety of sources, a few non-limiting examples include an incandescent lamp, xenon lamp, laser diodes, LED, laser or even a combination of two or more of these sources as well as other sources. Illumination sources 216 may operate in a pulsed, continuous, graduated, modulated, oscillating or other operation mode as well as a combination of two or more of these modes. The power and operational times of the sources are selected to avoid potential damage to the treated segment of skin. In some embodiments each of the illumination sources 216 may be packed in a cartridge-like packaging 224 detachable from the ergonomically designed, fitting-the-hand casing 204 of applicator 104. The cartridge like packaging of the illumination source advantageously allows different illumination sources to be used with the same applicator. Each of the cartridges, like illumination sources 216 packaging 224, may be mounted on springs or a flexible mounting enabling freedom of movement of the cartridge-like packaging 224 with light source 216 in respect to applicator casing 204 as shown by arrow 240 in FIG. 2B. This allows cartridge 224 with illumination sources 216 to follow skin/casing contour 244 when applicator 104 is translated (moved) over a segment of skin to be treated. Motion direction sensor 232 senses the applicator movement direction and provides a signal for proper switching of the light sources 216.

A cooling arrangement, possibly a fan (not shown) which may be placed at a section 236 located at the second end 212 of applicator 104. The fan removes the heat generated by the operation of electric and electronic circuits and lamps or LEDs of applicator 104 and enables normal operating conditions of the applicator.

FIG. 2C is a schematic illustration of a top view of the first end 208 of the exemplary embodiment of applicator 104. FIG. 2C shows the cartridge-like packaging 224 of light source 216, hair removal mechanism 220, and micro switches 228.

Figure 3A:
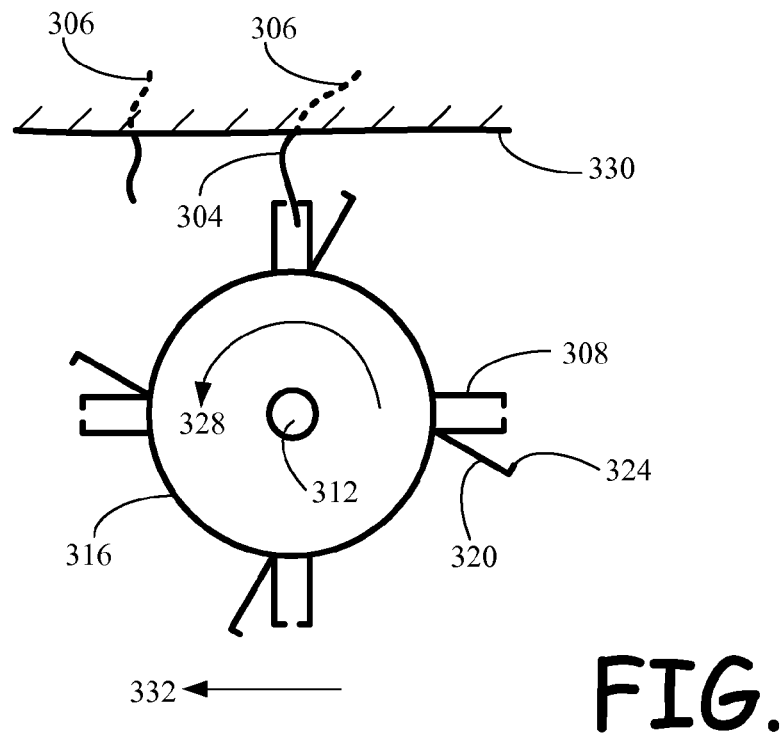
FIGS. 3A-3D are schematic illustrations of an exemplary embodiment of a hair removal mechanism of the applicator.
Figure 3B:
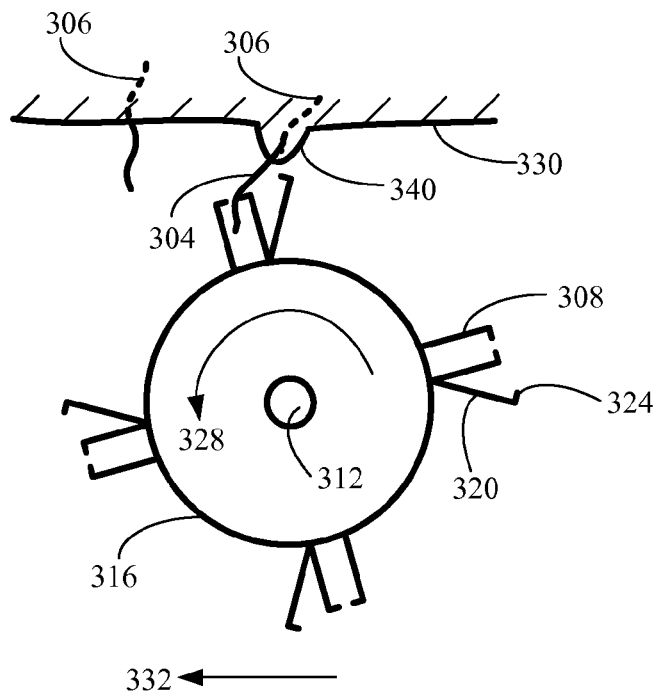

FIG. 3A illustrates a first state of the operation of an exemplary hair removal mechanism in operation. FIG. 3B illustrates a second state of operation of the exemplary hair removal mechanism in operation. In the exemplary embodiment illustrated in FIG. 3A, hair removal mechanism 220 may include at least one, and in some embodiments more than one, set of tweezers 308 attached to a holder 316 rotating around axis 312. Adjacent to tweezers 308 attached to the same axes is a lever 320 terminated by a blade 324. Alternatively, lever 320 may be rigidly coupled to tweezers 308 to ensure a constant follow-up after tweezers 308. There is a preset difference or offset between the location of tweezers 308 and the location of blades 324 of lever 320 with respect to skin 330. Typically, blade 324 would be located closer to skin 330 than tweezers 308. The difference in the location of blade 324 and tweezers 308 may be regulated according to the type of skin, hair, and particular treated segment of the subject casing.

For hair 304 removal, tweezers 308 are applied to skin 330. Holder 316 rotates in the direction indicated by arrow 328 and concurrently with rotation may move linearly on the surface of skin 330 in the direction indicated by arrow 332. As tweezers 308 continue to rotate to the second state, they pick-up at least one hair shaft or follicle 304 (FIG. 3B) and begin pulling it out of skin 330. A pulling force generated by the rotation of tweezers 308 and assisted by linear movement of holder 316 applied to hair shaft 304 pulls together with hair shaft 304, skin 330 surrounding the hair shaft and follicle. This force deforms skin 330 and forms a type of goose bump or goose pimple 340 protruding over the rest of the skin surface surrounding the follicle. Blade 324 cuts hair 304 (FIG. 3C) substantially close to the peak of goose bump 340. The pulling force is set to a particular tension with respect to the hair that is sufficient to impose a tension on the hair shaft but not enough to pull the hair shaft out of the skin.

Figure 4:
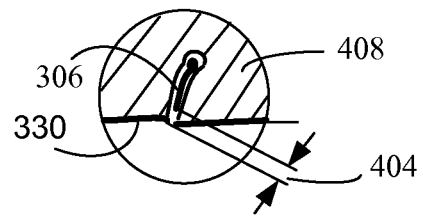
FIG. 4 is a magnified schematic illustration of a cut and retracted back hair follicle (shaft).

FIG. 4 is a magnified schematic illustration of a cut and retracted back hair shaft or follicle. Following the cut of hair shaft 304, skin 330 that formed goose bump 340, retracts or returns to its normal at rest state. The residuals 306 of hair shaft 304 retract to the original position. The residual 306 of hair shaft 304 retracts deeper than skin surface or stratum corneum 330, such distance being indicated by numeral 404 (FIG. 4), which marks the difference in the locations of the cut end of the residual 306 of the hair shaft 304 and skin surface 330. As can be seen in the figure, the end of the residual 306 resides substantially below skin surface 330. Numeral 408 indicates the underlying tissue.

Figure 3C:
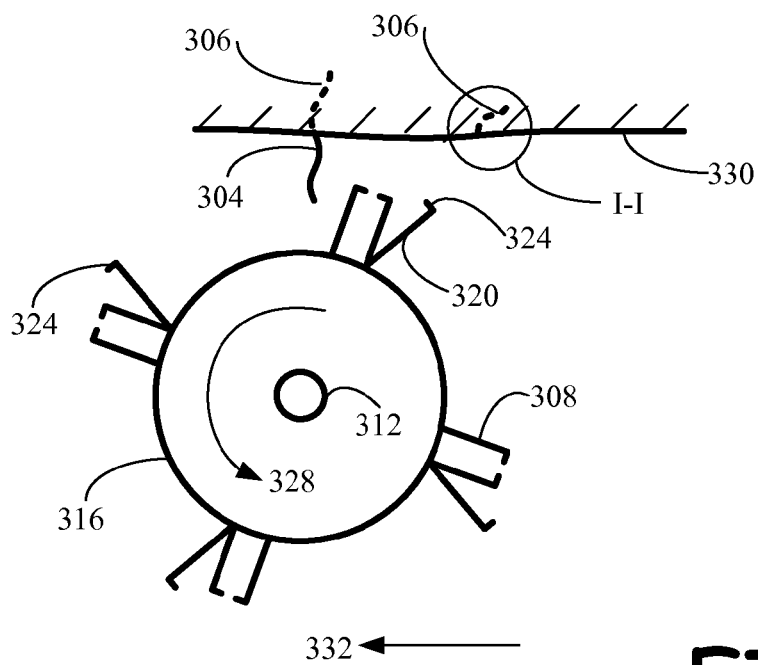
Figure 3D:
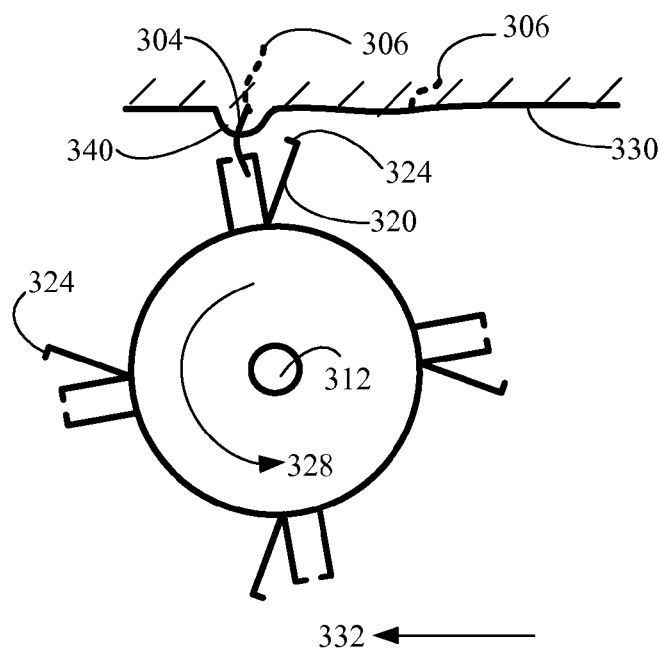

FIG. 3C illustrates a third state of the operation of the exemplary hair removal mechanism in operation. FIG. 3D illustrates a fourth state of operation of the exemplary hair removal mechanism in operation. Holder 316 (FIGS. 3C and 3D) continues to rotate in the direction indicated by arrow 328 and move linearly or in any other type of motion on the surface of skin 330 in the direction indicated by arrow 332. In the third state, tweezers 308 catch another hair shaft 304 and form bump 340 in the fourth operational state in a way similar to the one explained above. Next, hair 304 is cut in a way similar to the way that the previous hair shaft was cut. The tweezers 308 and blades 324 may be orientated in the same direction or staggered and oriented in different directions. When some of the tweezers 308 and blades 324 are oriented in different directions, the user may move back along the earlier treated skin segment and still be efficacious. When tweezers 308 and blades 324 are orientated in the same direction the user at the end of treatment stroke may rotate applicator 104 and move it in the opposite direction or simply reposition it to treat the next skin segment.

Alternatively, the hair removal mechanism 220 may be any one of the well-known mechanical hair removal mechanisms such as a razor, shaving, or an electric shaver such as for example, feminine electric shaver commercially available from Braun GmbH, Germany—model 3470 SOFTPERFECT. This model also includes other detachable heads of plucking and tweezing mechanisms. Similar or even the same mechanisms are also, of course, applicable to male hair removal/shavers. The illumination head/s may be attached and operate with a conventional epilator with only one head of either a shaver or epilator, or even a razor. The hair removal mechanism may be an exchangeable mechanism, where the mechanism most appropriate for the task is assembled on the applicator.

Illumination sources 216 (FIG. 2) may operate simultaneously with hair removal mechanism 220. However; they illuminate a different segment of skin from which hair removal mechanism 220 has already removed hair. Illumination destroys or weakens hair follicles and roots that are occasionally left, and should follow mechanical hair epilation. In order to synchronize the operation of illumination sources 216 with hair removal mechanism 220, a motion direction sensor, or even just a direction sensor (not shown) that switches between light sources 216 equips applicator 104. The direction sensor may be of different types, for example, a rotating wheel with a plurality of openings to modulate a source of light, a mechanical switch of any type, an optical mouse type direction sensor, an accelerometer, pressure sensors on the applicator 104 and others. Further, the direction sensor may determine displacement speed and trigger an off state if the displacement speed is lower than a target value or an on state if the displacement speed is above a target value. It will be appreciated that hysteresis may be applied in entering and exiting the on and off states. For instance, the threshold displacement speed to trigger the on state may be higher than the displacement speed to trigger the off state. In addition, the hysteresis effect may be obtained also by utilizing a time delay. For instance, once the on state is entered, a time delay can be set to prevent entrance into the off state during a desired delay. Likewise, once the off state is entered, another time delay can be utilized to prevent the on state from being immediately entered again. Activation of the illumination sources by direction sensors alleviates occasional skin burns or other treatment side effects, since illumination sources are operative only when the applicator moves over the skin in a minimum velocity. Moreover, it is possible to ensure that the appropriate illumination source illuminating the treated skin segment is activated based on the direction of advance of the applicator 104. Illumination sources 216 operate typically in continuous or pulse operation mode, but may also include any of the above-mentioned, or a combination of two or more of the above-mentioned operation modes, as well as other modes.

Figure 5:
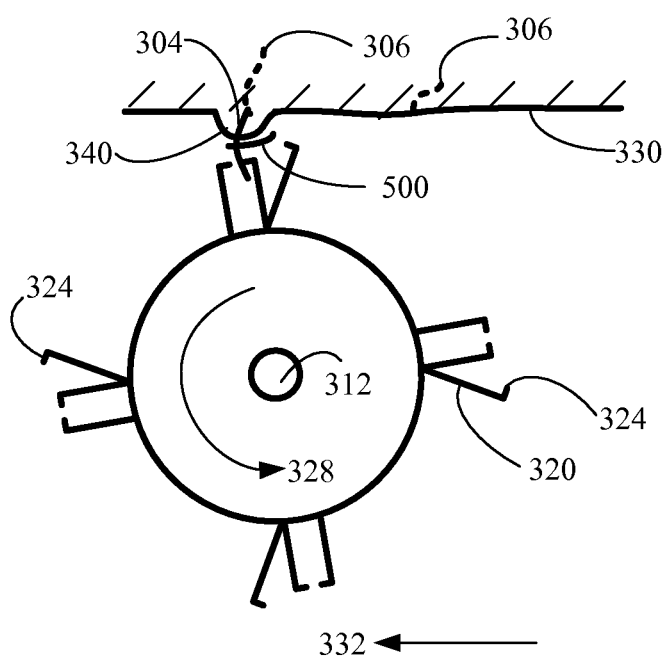
FIG. 5 is a schematic illustration of the second exemplary embodiment of the hair removal mechanism of the applicator.

FIG. 5 is a schematic illustration of the second exemplary embodiment of the hair removal mechanism. A comb type protective plate 500 protects skin 330 and especially bumps 340 from occasional damage by rotating blades 324 (FIG. 3). The comb type protecting plate 500 may be attached to the applicator 104 or held independently by a user. Blades 324 may be replaced by a fixed blade, which would cut hair 304 pulled by tweezers 308. In such embodiments, holder 316 in addition to rotation may have a linear motion. Alternatively, two comb-like blades linearly sliding with respect to each other may be implemented to cut the hair.

Figure 6A:
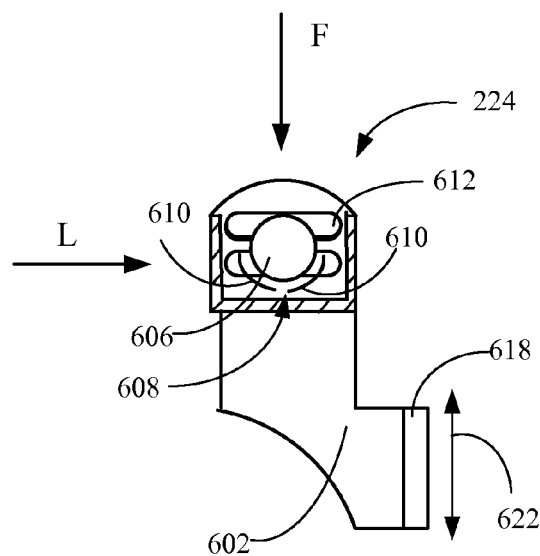
FIGS. 6A-6C are schematic illustrations of an exemplary embodiment of an illumination cartridge of the applicator.
Figure 6B:
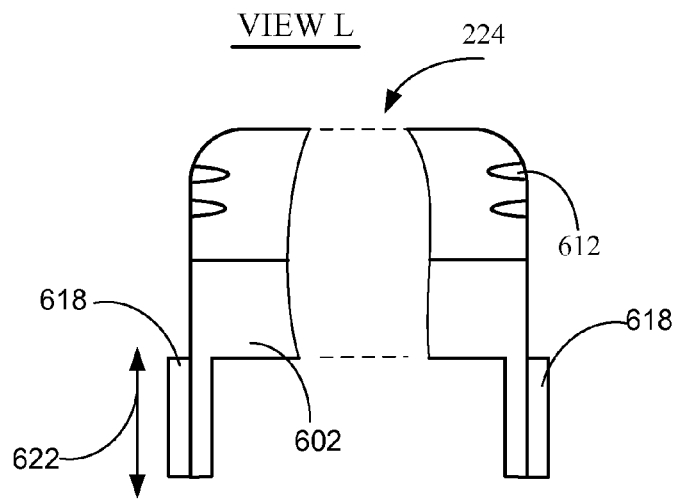
Figure 6C:
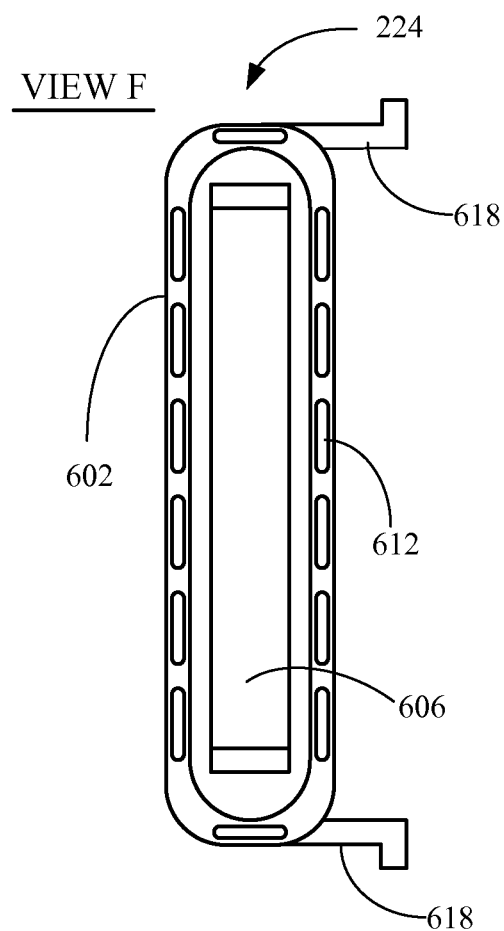

FIGS. 6A, 6B and 6C, collective referred to as FIG. 6, depict a schematic illustration of an exemplary embodiment of an illumination cartridge of the applicator. Enclosure 602, which may be constructed of plastic, of cartridge 224 incorporates a source of illumination such as an incandescent lamp, xenon flash lamp, laser diode, LED, laser or a combination of two or more of these sources as well as others. FIG. 6A illustrates cartridge 224 with a xenon lamp 606 and a reflector 610 configured to collect a large part of the irradiance emitted by the xenon lamp 606 and direct it towards the treated segment of skin.

Plastic enclosure 602 of cartridge 224 includes two guides 618 supporting easy cartridge 224 insertion and cartridge movement along a direction indicated by arrow 622. The disclosed cartridge construction allows the treated skin segment contour 244 to be easily followed, as shown in FIG. 2B, and uniform illumination maintained of the treated skin segment. In one embodiment, cartridge 224 movement is utilized to replace micro switches 228. This may be enabled by allowing the pressed-in cartridge 224 to activate electrical and electronic circuits of applicator 104 in a mode similar to that of micro switches 228. Alternatively, guides 618 may be metalized and their descent would come in contact with a conductor and thereby close an electric circuit. It is also possible to have a section of guides to be transparent and another section opaque. Linear movement of such guide can modulate a light beam and activate or deactivate the electrical and electronic circuits of applicator 104. As will be explained below, additional methods of replacing micro switches by other sensing and switching mechanisms can be used.

Reflector 610 is shown to be constructed from two similar halves enabling free airflow for cooling lamp 606. Alternatively, a reflector formed as an integral body with respective air intake openings 608 may be used. Reflector openings 608 cooperate with respective air vents or air intake openings 612 enabling convective cooling of lamp 606 or LEDs (not shown).

Figure 7A:
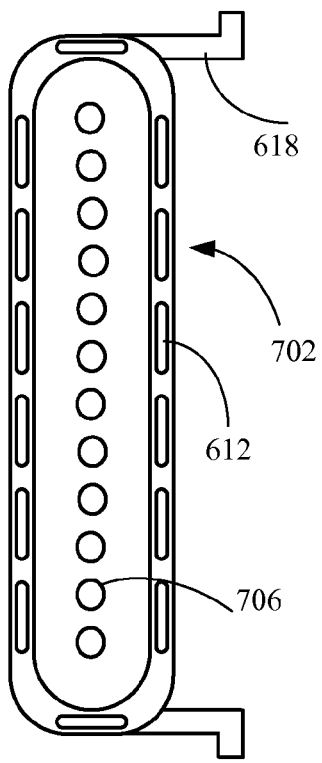
FIGS. 7A-7B are schematic illustrations of additional exemplary light source configuration of the applicator.
Figure 7B:
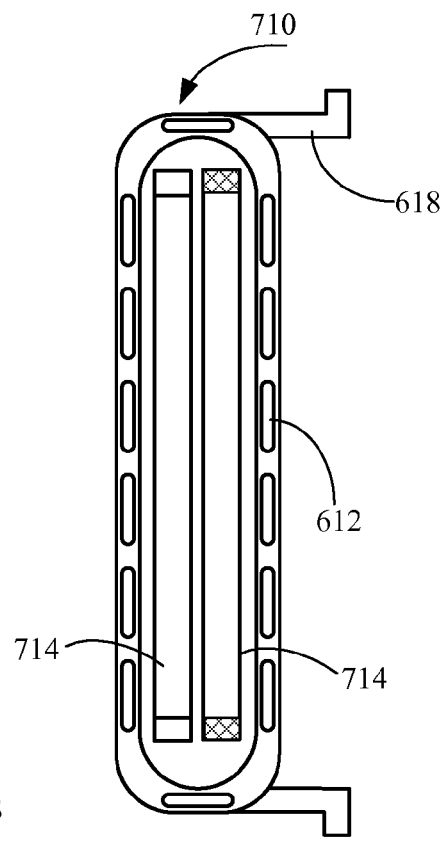

FIGS. 7A and 7B, collectively referred to as FIG. 7, depict a schematic illustration of another exemplary light source configuration of the applicator. FIG. 7A illustrates cartridge 702 similar to cartridge 224 with a plurality of LEDs 706. Each of LEDs 706 may emit a single wavelength or a plurality of wavelengths. LEDs 706 are configured to illuminate the treated segment of skin by a flux having relatively uniform flux distribution. FIG. 7B illustrates a cartridge 710 with two light sources 714, such as Xenon or other type lamps. Sources 714 may be identical sources or different light sources. Their illumination fields may overlap and they may be configured to get a desired spectrum and illumination distribution on the treated skin segment. Sources 714 may be operated simultaneously, at different or partially overlapping periods and at different operating modes e.g. pulsed. continuous or otherwise.

The described applicator architecture supports different combinations of hair removal mechanisms and illumination sources. Accordingly, a particular combination of the exchangeable hair removal mechanism and illumination sources may determine the mode of operation of the applicator. The mechanical hair removal mechanisms may be selected, for example, from a rotary-based tweezing epilator, spring type epilator, razor, or electric shaver. The illumination source may be, for example, selected from continuous or pulse operating sources as well as the other above-listed modes, sources providing a desired spectrum and illumination distribution on the treated skin segment. There may be a mix of sources operating simultaneously or at partially overlapping periods. This selection provides a wide array of combinations that may be adapted for different skin treatments.

Figure 8A:
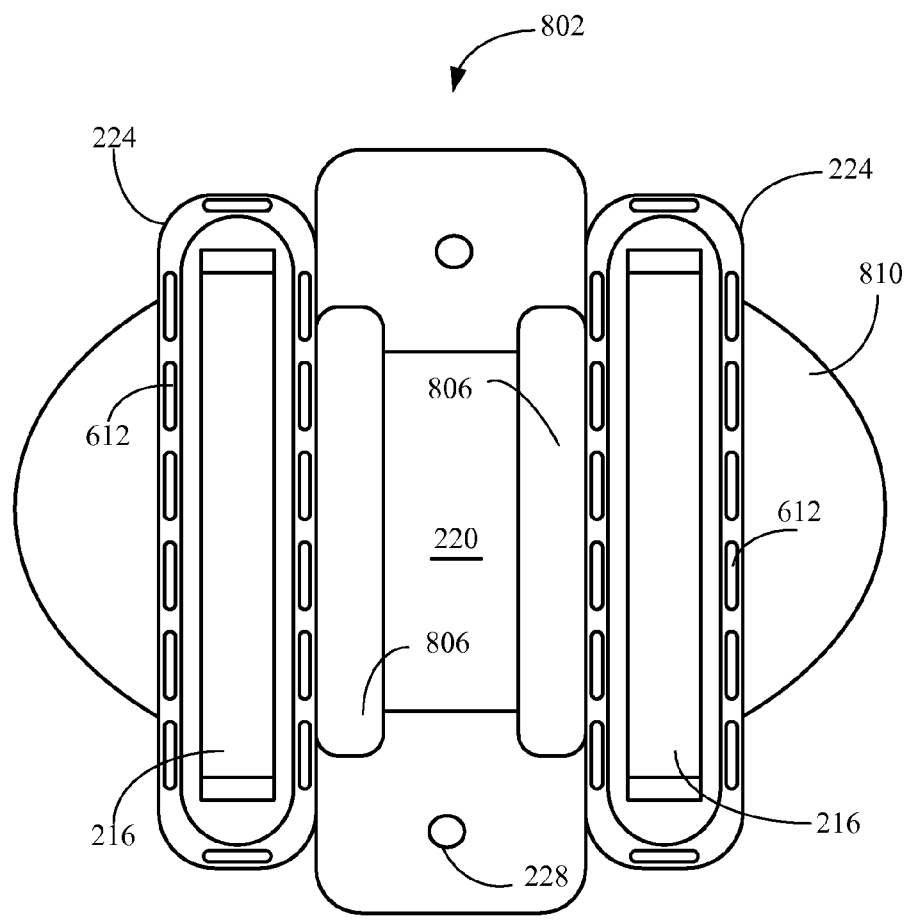
FIGS. 8A-8E are schematic illustrations of the third exemplary embodiment of the applicator.
Figure 8B:
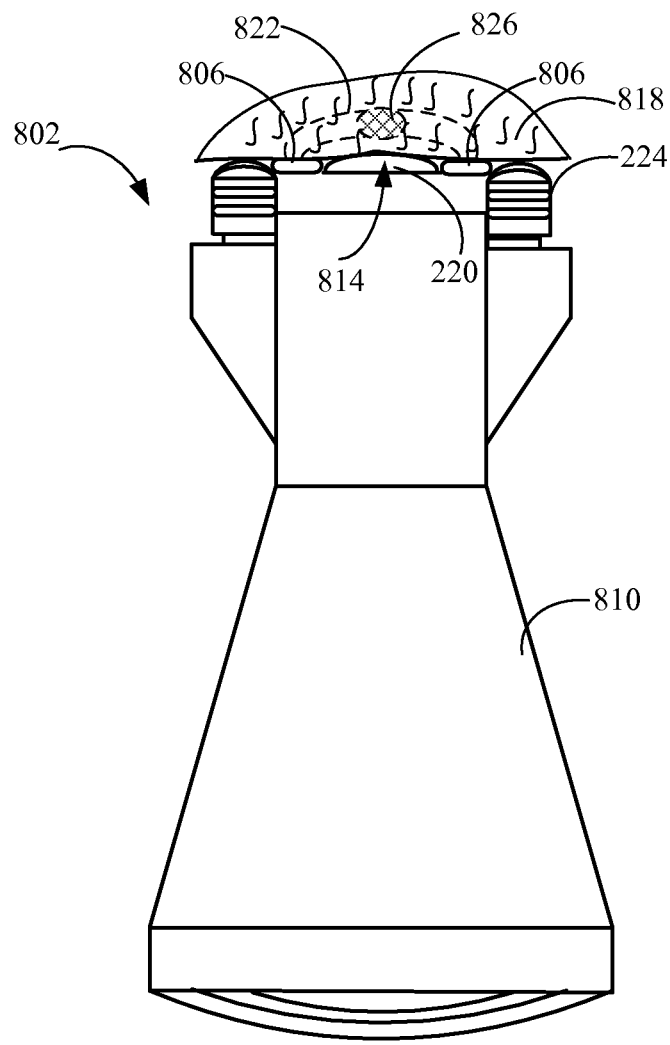
Figure 8C:
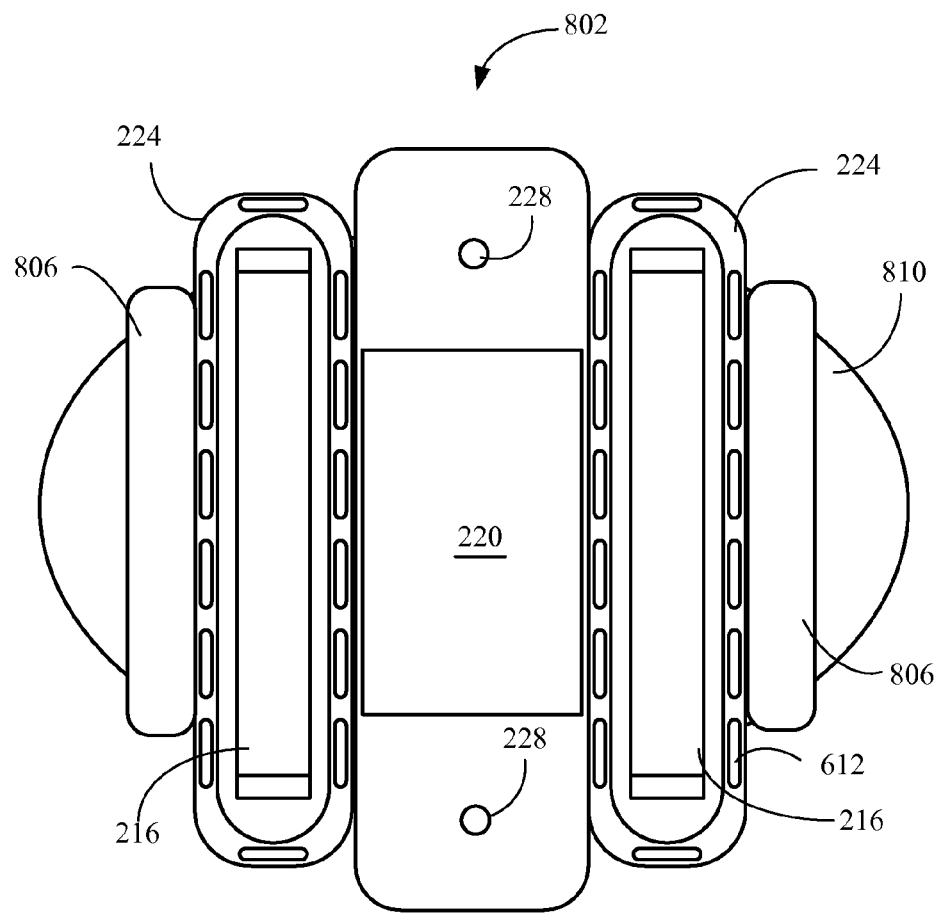
Figure 8D:
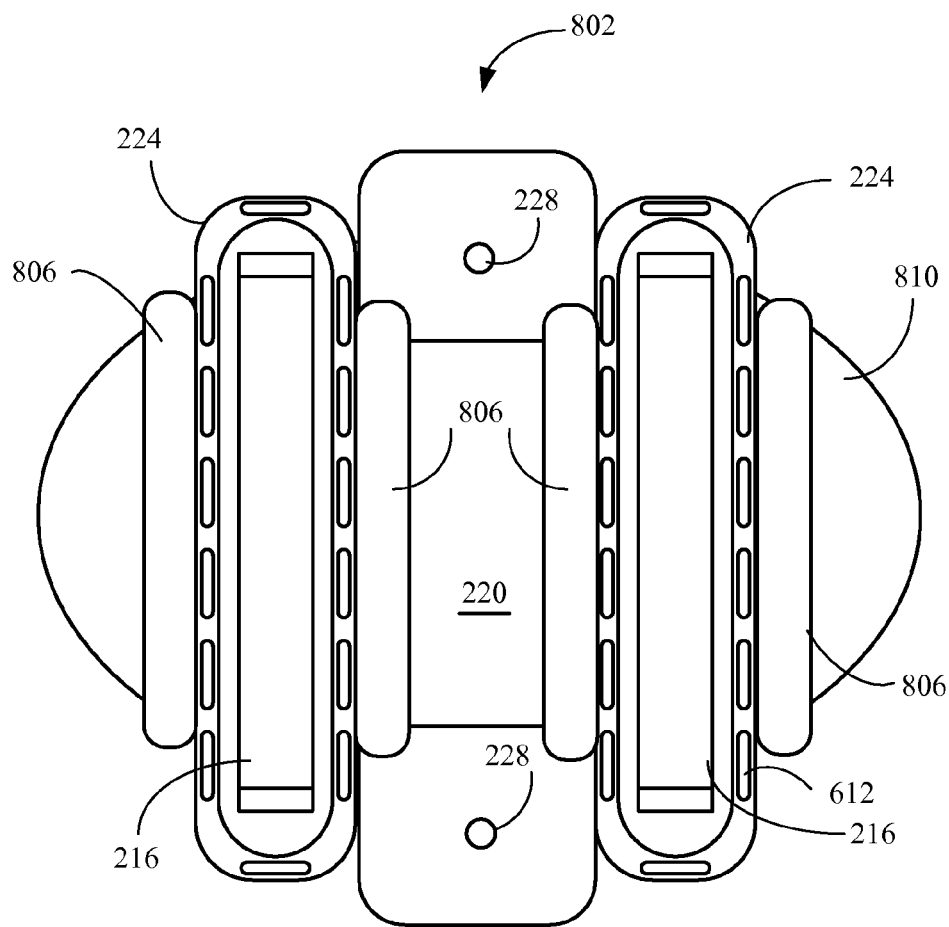
Figure 8E:
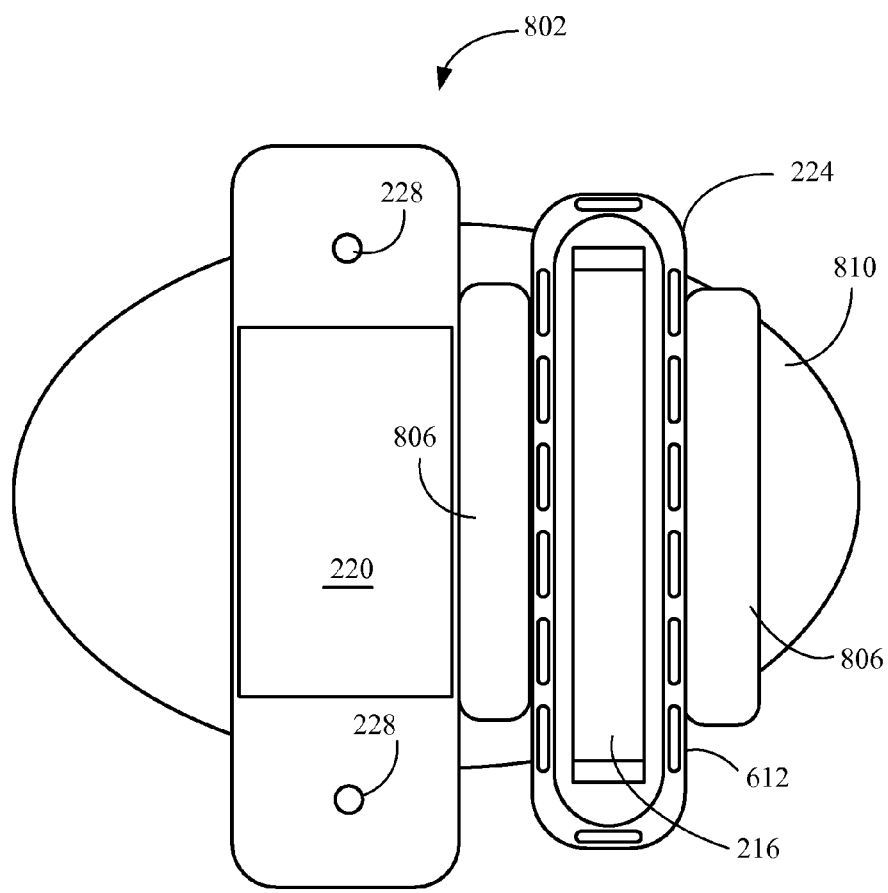

FIGS. 8A-8D illustrate variations in a third embodiment, with the figures being referred to collectively as FIG. 8. FIG. 8A depicts an additional embodiment in which the applicator 802 includes one or more RF electrodes 806 configured to contact the treated segment of skin and provide RF energy to the segment of skin 814 (FIG. 8B) located between electrodes 806, The RF energy is generated by an RF generator located in applicator casing 810 (FIG. 8A). Typically, the electrical and electronic circuits of applicator 802 include circuits that enable power to one or more illumination sources and RF sources. When RF electrodes 806 touch the subject skin (as illustrated in FIG. 8B), they provide a path for the current of the electrical and electronic circuits of applicator 802. An impedance sensing mechanism senses the impedance change from an infinite value to a measurable finite value and activates supply of RF energy having a magnitude sufficient to produce a desired skin or tissue treatment effect. RF induced current flows through tissue 818 as shown by lines 822 between electrodes 806 heating tissue volume schematically indicated by reference numeral 826. Thus, the use of an applicator is safer than mechanical switching, since little or no RF is emitted if there is no contact of RF electrodes 806 and the skin. The electrical response to the impedance changes is faster than mechanical switching and if one electrode loses contact with the skin, the RF emission is instantly switched-off. (Generally, a very low level of RF power may continue to be emitted in order to be able to activate the illumination sources and RF energy when contact with the skin will be once again established.) Optionally, applicator 802 may have an ON-OFF switch to switch off applicator 802 completely. FIG. 8C is another schematic illustration of the third exemplary embodiment of the applicator. In this embodiment, RF electrodes 806 are located at the external side of the cartridges 224 and FIG. 8D illustrates an additional of embodiment of the applicator, where RF electrodes 806 are located on both sides of the cartridges 224. FIG. 8E illustrates still a further embodiment of the applicator 802, where only one cartridge 224 is used with RF electrodes 806 located on both sides of the cartridge 224.

All earlier described applicator 104 (FIG. 2) components, such as a hair removal mechanism, illuminators and their functionality are mutatis mutandis applicable to applicator 802.

Figures 9A, 9B:
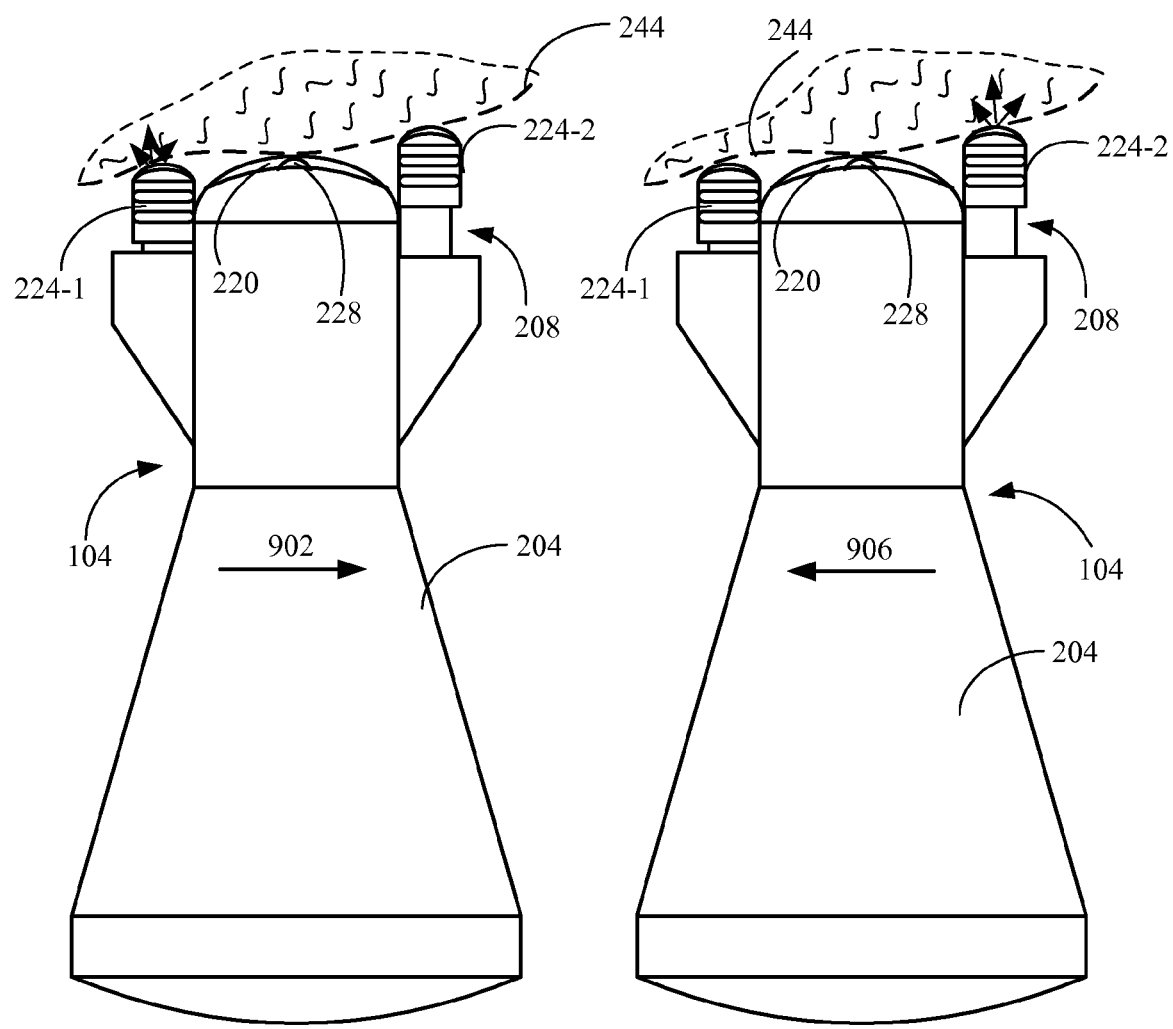
FIG. 9 is a schematic illustration of a hair removal treatment using the first exemplary embodiment of the present applicator.

FIGS. 9A and 9B, collectively referred to as FIG. 9, depicts a schematic illustration of a hair removal treatment using the first exemplary embodiment of the present applicator. The first end 228 of applicator 104 is applied to skin 244. This applies slight pressure on micro switches 228 and therefore hair removal mechanism 220 and appropriate illumination sources are enabled. (Generally, both the hair removal mechanism and the illumination source may be enabled by other mechanisms independent of a micro switch mechanism). The user of the applicator translates applicator 104 in a scanning motion in the first direction indicated by arrow 902 (FIG. 9A) from one segment of skin 244 to another skin segment. During the translation, hair removal mechanism 220 removes hair from the treated segment of skin 244. A motion direction sensor senses the movement direction and activates trailing illumination source located in cartridge 224-1 to illuminate a skin segment from which the hair was removed. Continuous illumination flux produced by the trailing illumination source 224-1 heats the skin segment from which earlier hair was attempted to be removed mechanically, weakens and perhaps destroys the hair follicles and bulbs. Typical useful values of the illumination flux would have a value in the range of 0.5 $J/cm^2$ to 20 $J/cm^2$. In addition to destroying hair follicles and bulbs, illumination flux accelerates skin-healing effect.

When applicator 104 moves in a second direction indicated by arrow 906 (FIG. 6B), hair removal mechanism 220 functions in a similar way and removes hair from the mechanically treated skin segment. The motion direction sensor senses the changes in the direction movement and switches off illumination source located in cartridge 224-1 (it becomes a leading illumination source that is now turned off) and turns on what is now the trailing illumination source located in cartridge 224-2 to illuminate a skin segment from which the hair has been removed. Illumination sources located in cartridges 224-1 and 224-2 may operate simultaneously (concurrently) with hair removal mechanism 220. However, illumination sources located in cartridge 224-1 and 224-2 operate on different segments of skin 244 than the hair removal mechanism 220 operates. Illumination sources may operate in a continuous mode and their power set to cause a desired skin effect and prevent skin burns. An optional temperature sensor may be used to continuously measure skin temperature and accordingly deactivate the RF and/or light sources.

As noted the illumination flux produced by the trailing illumination source located in cartridge 224-1 generates the effects described above of stunning the hair shaft growth as well as skin-healing effect. The effect may be further enhanced by proper selection of the illuminating wavelength and intensity.

The trailing and leading illumination sources typically, may be operative to generate different flux values most appropriate for getting the desired effect. When illumination sources are LED based sources, such as shown in FIG. 7A, the trailing and leading illumination sources may be operative to emit different wavelengths more suitable for getting the desired effect. Generally, as previously explained, the illumination source cartridge may be constructed to include more than one lamp to operate them at different power levels or emit energy at different spectrums, as would be most appropriate for getting the desired treatment effect.

Figure 10:
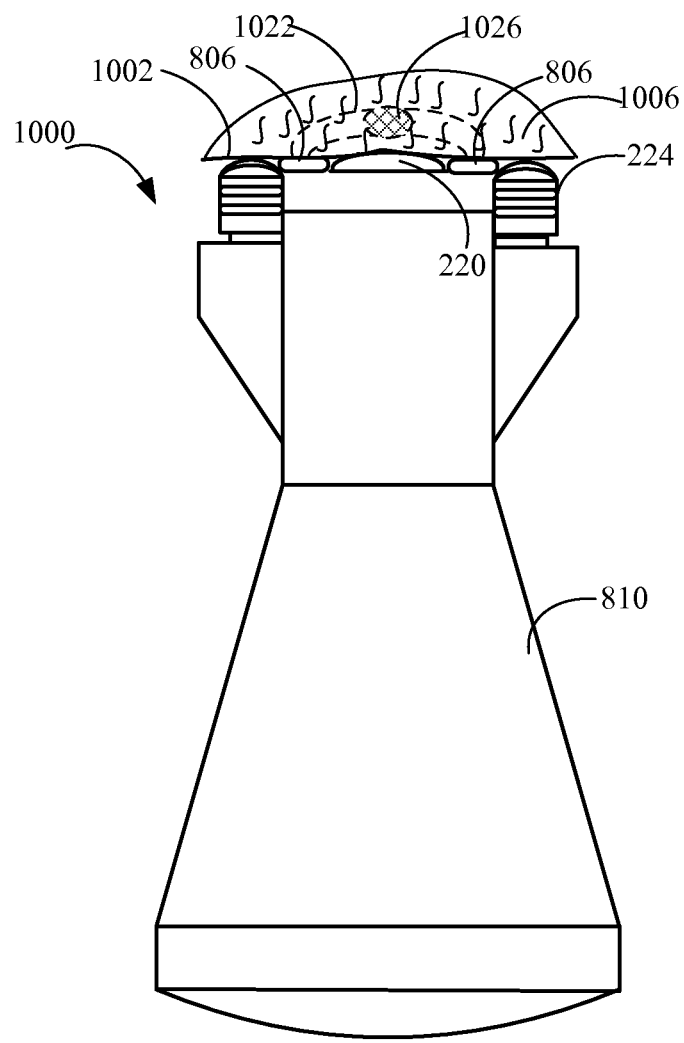
FIG. 10 is a schematic illustration of a hair removal treatment using the second exemplary embodiment of the present applicator.

FIG. 10 is a schematic illustration of a hair removal treatment using another exemplary embodiment of the present applicator. Applicator 1000 is applied to skin 1002 such that it forms a contact between RF electrodes 806 and skin 1002. Impedance sensing mechanism senses the change in the impedance from infinity to a certain value and activates electric and electronic circuits of applicator 1000. Thus, the impedance sensing mechanism can replace the micro switch mechanism described earlier, although both mechanisms may be combined to provide enhanced safety in the treatment. Mechanical hair removal mechanism physically removes the hair. RF induced current shown by lines 1022 heats tissue 1006 and in particular volume 1026, weakens or even destroys residual hair follicles and bulbs. The user of the applicator translates applicator 1000 in a scanning motion from one segment of skin 1002 to another skin segment and heats respective tissue volumes 1026. In the course of the translation, hair removal mechanism 220 removes hair from the segments of skin 1002 located over the heated tissue volumes. Motion direction sensor 232 (FIG. 2A) senses the movement direction and activates trailing illumination source 224 to illuminate a skin segment from which the hair was removed. Illumination flux produced by the trailing illumination source 224 weakens the hair follicle and hair shaft, and to some extent, heats the skin and destroys the remaining hair follicles and bulbs not removed by mechanical means. In addition to destroying hair follicles and bulbs, illumination flux accelerates skin-healing effect. All disclosed above illumination flux and wavelength variations and illumination source switching are mutatis mutandis applicable to the present embodiment that uses RF to heat deeper tissue layers.

Figure 11:
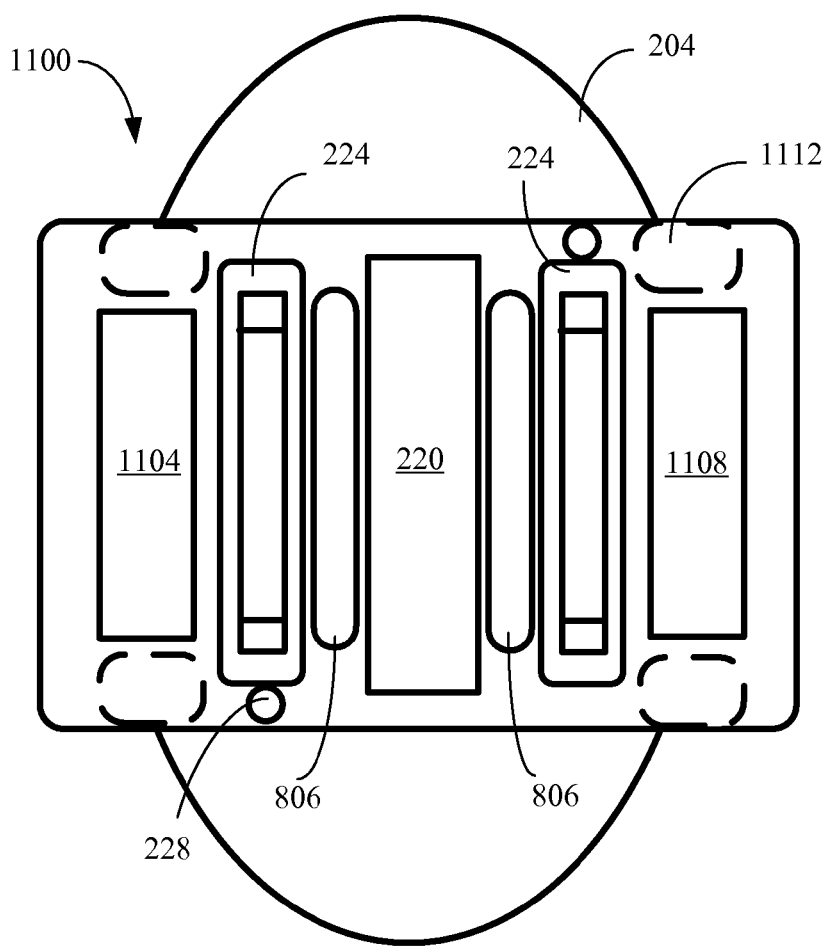
FIG. 11 is a schematic illustration of the forth exemplary embodiment of the present applicator.

The skin treatment results may be improved by proper preparation of the skin segment to be treated. Post treatment rash may be reduced by application of a solution, such as creams, lotions or other liquid or powder. FIG. 11 is a schematic illustration of the fourth exemplary embodiment of the present applicator. Applicator 1100, in addition to the earlier described hair removal mechanism 228, illumination sources 224, RF electrodes 806, and micro switches 228 includes a skin and hair pre-treatment device 1104 and a skin and hair post treatment device 1108. The skin and hair pre-treatment device 1104 may be operative to clean by spray or similar solution a segment of skin to be treated. The skin and hair post treatment device 1108 may be operative to disperse over the treated segment of the skin a cream or solution reducing irritation that the treatment may occasionally cause to the skin. Optional variable length spacers 1112 may be used to maintain a desired gap between the location of the hair removal mechanism and the skin.

Typically, any one of the applicators described will be electrically driven, i.e. by a drive rotating the hair removal mechanism and operating other units of the applicators. Alternatively, the applicator may be configured such that the sliding movement over the skin of the subject would provide a rotational movement to the hair removal mechanism.

Application of the method enables almost a hair free skin area to be achieved due to mechanical hair removal, and retard or completely eliminate hair re-growth enabled by (concurrent, or subsequent, or prior to mechanical hair removal) RF application and skin illumination. Skin healing process is accelerated by selection of proper skin illumination wavelengths.

Figures 12A, 12B:
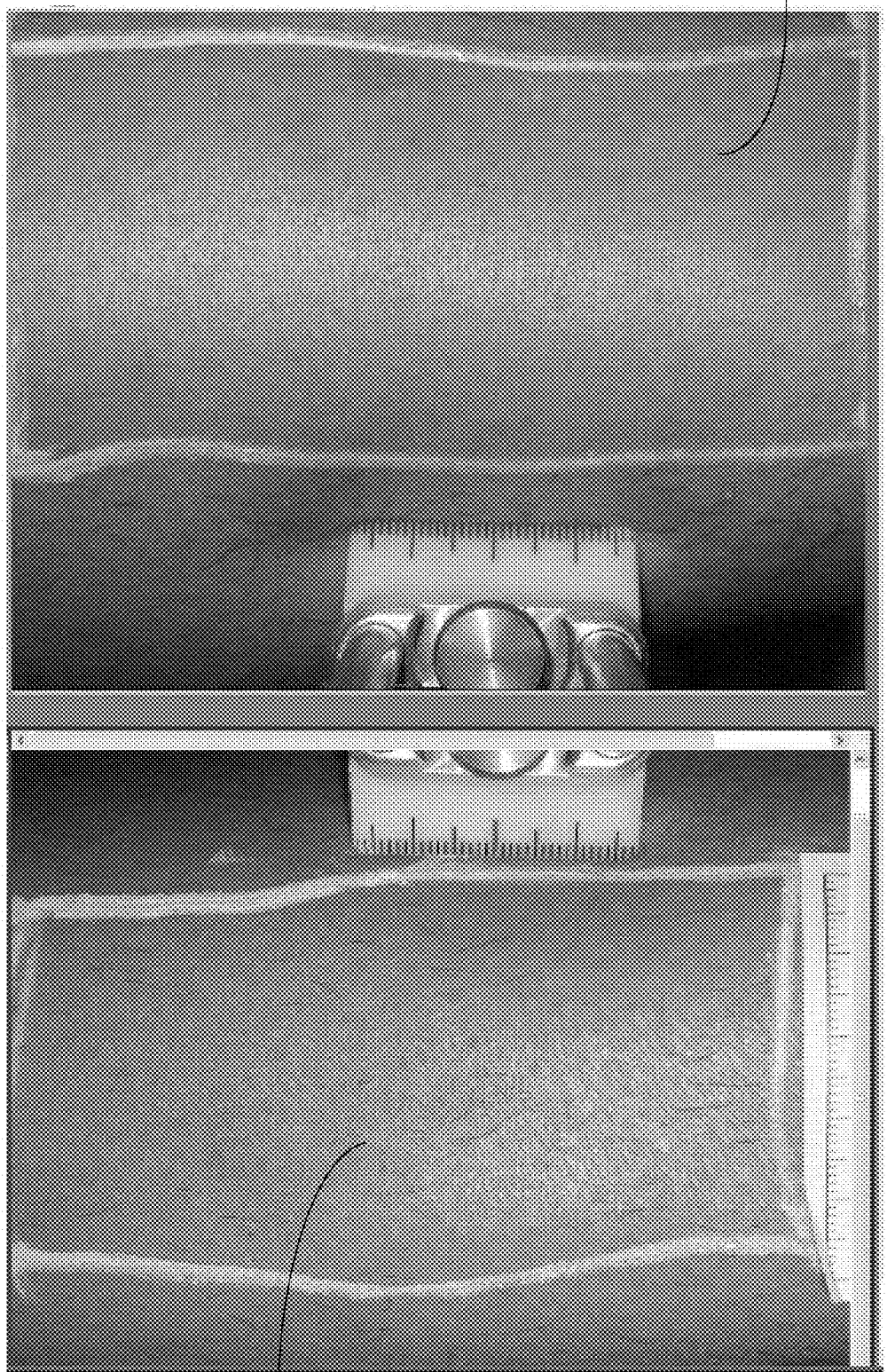
FIG. 12 is a photographic image of a segment of a subject skin treated by the present method and an image of a untreated segment (control segment) of a subject skin.

FIG. 12 is a photographic image of a segment of a subject skin treated by the present method and an image of non-treated segment (control) of a subject skin. The treated segment 1206 does not contain even residual hair. The non-treated segment 1202 is shown for comparative purposes.

Several embodiments have been described using detailed descriptions thereof that are provided by way of example and are not intended to be limiting. The described embodiments comprise different features, not all of which are required in all embodiments. Some embodiments utilize only some of the features or possible combinations of the features. Variations of embodiments that are described and embodiments comprising different combinations of features noted in the described embodiments will occur to persons skilled in the art.

It will be appreciated by persons skilled in the art that the follow claims are thus not limited to the disclosed embodiments, features, functions, etc. but that rather the claims may encompass additional embodiments.

What is claimed is:

1. An applicator for hair removal, the applicator comprising:
at least two illumination sources being detachable from an applicator casing, the illumination sources configured to follow a treated skin segment contour and provide illumination with one or more wavelengths, and at least one being a leading illumination source and at least one being a trailing illumination source;
an exchangeable mechanical hair removal mechanism; and
one or more sensors, with at least one of the sensors being a motion direction sensor and one of the sensors being an impedance sensing mechanism;
at least two RF electrodes, the RF electrodes configured to provide RF energy to a segment of skin being in contact with the RF electrodes and to induce current which heats the skin so as to weaken or destroy hair follicles and bulbs;
wherein the hair removal mechanism is located between the at least two illumination sources, and at least one of the RF electrodes is arranged between at least one of the illumination sources and the hair removal mechanism, such that when the applicator is displaced in a direction over a subject's skin at least one illumination source precedes the hair removal mechanism and at least one illumination source succeeds the hair removal mechanism; and wherein the at least one motion direction sensor is operative to:
activate at least one of the illumination sources according to the applicator displacement direction; and
de-activate at least one of the illumination sources according to the applicator displacement direction;
such that only the at least one trailing illumination source is activated relative to the applicator displacement direction.

2. The applicator according to claim 1, wherein the exchangeable mechanical hair removal mechanism is a set of tweezers and a lever terminated by a blade, wherein the lever is attached to the same axes as the tweezers are attached.

3. The applicator according to claim 1, wherein at least one of the illumination sources includes at least one of a group of illumination sources comprising an incandescent lamp, xenon lamp, laser diode, LED, laser or a combination of two or more of these sources.

4. The applicator according to claim 1, wherein the at least two illumination sources operate in an operation mode selected from the group of operation modes comprising a continuous mode and a pulse mode, and wherein the illumination sources are interchangeable and removable sources.

5. The applicator according to claim 1, wherein the illumination sources are cartridges that include two guides for insertion into the applicator casing and have a freedom of linear movement along the two guides with respect to the applicator casing, and when the illumination sources are pressed-in they activate electrical and electronic circuits of the applicator.

6. The applicator according to claim 1, wherein at least one of the sensors is one of a group of sensing mechanisms comprising direction sensors, micro switches, and temperature sensors.

7. The applicator according to claim 1, further comprising a cooling arrangement located proximate to the exchangeable mechanical hair removal mechanism of the applicator for cooling the electric and electronic circuits of the applicator and illumination sources.

8. The applicator according to claim 1, wherein the motion direction sensor determines displacement speed of the applicator and triggers an on and off state, and a hysteresis is applied in entering and exiting the on and off states, wherein the hysteresis means different threshold displacement speeds trigger the on state and the off.

9. The applicator according to claim 1, wherein at least two RF electrodes are arranged between at least one of the illumination sources and the exchangeable mechanical hair removal mechanism.

10. The applicator according to claim 1, wherein each of the illumination sources is arranged between at least one RF electrode and the exchangeable mechanical hair removal mechanism.

11. The applicator according to claim 1, wherein each of the illumination sources is arranged between at least a pair of RF electrodes, and the hair removal mechanism is arranged between at least two pairs of RF electrodes.

12. The applicator according to claim 1 wherein the illumination sources when pressed-in activate electrical and electronic circuits of the applicator.

13. The applicator according to claim 1 further comprising at least one sensing mechanism, the mechanism activates supply of RF energy to RF electrodes.

14. The applicator according to claim 1 further comprising skin and hair pre-treatment and post-treatment devices, wherein the skin and hair pre-treatment device is operative to clean by spray or similar solution the skin to be treated and the skin and hair post-treatment device is operative to disperse over a treated segment of skin a cream or lotion reducing skin irritation.

15. The applicator according to claim 1, wherein the motion direction sensor is operative toc12 sense the applicator movement direction and activate trailing illumination source to illuminate a skin segment from which the hair was mechanically removed to further weaken the hair follicle and hair shaft and destroy the remaining hair follicles and shafts not removed by mechanical hair removal mechanism.

16. The applicator according to claim 1, wherein the mechanical hair removal mechanism removes hair weakened or destroyed by the RF electrodes.

17. The applicator according to claim 1, wherein the leading illumination source and trailing illumination source generate different flux values.

* * * * *